United States Patent [19]

Crawford

[11] 4,111,958

[45] Sep. 5, 1978

[54] ASCORBIC ACID SYNTHESIS

[75] Inventor: Thomas C. Crawford, Norwich, Conn.

[73] Assignee: Pfizer Inc., New York, N.Y.

[21] Appl. No.: 803,020

[22] Filed: Jun. 3, 1977

[51] Int. Cl.$^2$ .................. C07D 307/32; C07D 319/04
[52] U.S. Cl. .............................. 260/340.7; 260/343.7
[58] Field of Search ........................... 260/340.7, 343.7

[56] References Cited

PUBLICATIONS

Kitahara et al., Agr. Biol. Chem. 38(11), 2189–2190, 1974.

*Primary Examiner*—Cecilia M. Jaisle
*Attorney, Agent, or Firm*—Francis X. Murphy; Charles J. Knuth; Peter C. Richardson

[57] ABSTRACT

Ascorbic acid is prepared from a 1,4-lactone selected from gulono-1,4-lactone, galactono-1,4-lactone, idono-1,4-lactone and talono-1,4-lactone by a process comprising protection of the hydroxyl groups of the lactone so as to form an intermediate having a free hydroxyl group at either, but not both, the 2- or 3-position, oxidizing this free hydroxyl group to a keto group and hydrolyzing the oxidized intermediate to remove the hydroxyl-protecting groups.

26 Claims, No Drawings

ASCORBIC ACID SYNTHESIS

BACKGROUND OF THE INVENTION

This invention relates to a novel process for preparing ascorbic acid. L-ascorbic acid, or Vitamin C, is required in the human diet and is widely sold in tablet form and as an additive in various foodstuffs to meet this need and also as an antioxidant. In all animals except primates and guinea pigs L-ascorbic acid is biosynthesized from D-glucose. The final step in this biosynthesis is the enzymatic conversion of L-gulono-1,4-lactone to L-ascorbic acid. British Pat. No. 763,055 discloses the conversion of L-gulono-1,4-lactone to L-ascorbic acid in about 40% yield by the use of an enzymatic oxidation system.

Attempts to effect the direct conversion of L-gulono-1,4-lactone to L-ascorbic acid by chemical means have been only partly successful, since over-oxidation and degradation reactions produce undesirable by-products. However, low yields of L-ascorbic acid have been produced. For example, Berends and Konings, Rec. Trav. Chim. des Pays-Bas, 74, 1365 (1955) disclose the use of Fentons reagent to give about a 10% yield of L-ascorbic acid. The most successful and common method of producing L-ascorbic acid is based on a multi-step synthesis from D-glucose going through sorbose and 2-ketogulonic acid as intermediates. Many improvements in the original sorbose method of Reichstein and Grussner, Helv. Chim. Acta., 17, 311 (1934) have been made. D-ascorbic acid may be used as an antioxidant in foodstuffs.

Derivatives of L-gulono-1,4-lactone are known in the art. For example, Matsui et al. have prepared 2,3:5,6-di-O-isopropylidene-L-gulono-1,4-lactone, 3,5-O-benzylidene-L-gulono-1,4-lactone, 2,6:3,5-di-O-benzylidene-L-gulono-1,4-lactone (Yakugaku Zasshi 86, 110 (1966)), and 2,3,5,6-tetrabenzoyl-L-gulono-1,4-lactone has been prepared by Kohn et al. (J.A.C.S., 87, 5475 (1965)). Similar compounds derived from D-gulono-1,4-lactone are also known including 2,3:5,6-di-O-isopropylidene-D-gulono-1,4-lactone, 2,3-O-isopropylidene-D-gulono-1,4-lactone and 5,6-O-isopropylidene-D-gulono-1,4-lactone (Hulyalkar et al., Can. J. Chem., 41, 1898 (1963)). Other compounds include 2,3,5,6-tetra-O-trimethylsilyl-D-gulono-1,4-lactone (Meguro et al., Agr. Bio. Chem., 36, 2075 (1972)), 2,3,5,6-tetra-O-acetyl-D-gulono-1,4-lactone (Ness et al., J.A.C.S., 73, 4759, (1951)) and 2,3,5,6-tetra-O-benzoyl-D-gulono-1,4-lactone (Kohn et al., J.A.C.S., 86, 1457 (1964)). Similar derivatives of gulonic acid and gulonamide have been prepared. Similar derivatives of the other 1,4-lactones are also known. Prior to the present process, the oxidation of partially protected 1,4 lactones is not known to have been described nor are such compounds known to have been employed as intermediates in the preparation of ascorbic acid.

SUMMARY OF THE INVENTION

The present invention provides a novel process for the preparation of ascorbic acid from a 1,4 lactone selected from gulono-1,4-lactone, galactono-1,4-lactone, idono-1,4-lactone and talono-1,4-lactone. L-ascorbic acid is prepared from lactones of the L-series and D-ascorbic acid results from lactones of the D-series. The lactone is first reacted with a hydroxyl-protecting reagent to form a hydroxyl-protected intermediate wherein one of the hydroxyl groups located at the 2- and 3-positions of the ring is protected while the other remains as a free hydroxyl group. The free hydroxyl group at the 2- or 3-position of this protected intermediate is then oxidized to a keto group and the resulting compound subjected to hydrolysis until substantial conversion to ascorbic acid has occurred.

In one embodiment of this invention, this process may be effected by (a) contacting a 1,4-lactone selected from gulono-1, 4-lactone, galactono-1,4-lactone, idono-1,4-lactone and talono-1,4-lactone with about three equivalents of a hydroxyl-protecting reagent per mole of 1,4-lactone; (b) contacting the resulting intermediate having a free hydroxyl group at the 2- or 3-position with an oxidizing agent effective to convert said hydroxyl group to a keto group and (c) hydrolyzing the compound formed in step (b) until conversion to ascorbic acid is substantially complete. Preferred hydroxyl-protecting reagents for this process include trialkylsilyl halides and dialkylsilyl halides, wherein each alkyl is of 1 to 6 carbon atoms; alkanoic anhydrides of 3 to 8 carbon atoms, alkanoyl halides of 2 to 6 carbon atoms; aroyl halides wherein said aroyl is benzoyl, naphthoyl or monosubstituted benzoyl, wherein said substituents are alkyl of 1 to 6 carbon atoms, alkoxy of 1 to 6 carbon atoms, halo or nitro; dialkyl ketones, wherein each alkyl is of 1 to 6 carbon atoms; alkyl aldehydes of 2 to 8 carbon atoms; and triphenylmethyl halides.

Ascorbic acid may also be prepared by (a) contacting a 1,4-lactone selected from gulono-1,4-lactone and idono-1,4-lactone in the presence of an acid catalyst having a $pk_a$ of less than about 2.5 with at least about two equivalents of a hydroxyl-protecting reagent per mole of 1,4-lactone, said reagent being selected from an alkyl aldehyde of 2 to 8 carbon atoms; an aryl aldehyde, an arylakyl aldehyde and an arylalkenyl aldehyde, wherein said aryl is phenyl, monosubstituted or disubstituted phenyl, wherein said substituents are alkyl of 1 to 6 carbon atoms, alkoxy of one to six carbon atoms, halo or nitro, and said alkyl and alkenyl are each of 2 to 4 carbon atoms; (b) contacting the resulting intermediate having a free hydroxyl group at the 2-position with an oxidizing agent effective to convert said hydroxyl group to a keto group and (c) hydrolyzing the compound formed in step (b) until conversion to ascorbic acid is substantially complete. Preferred hydroxyl-protecting reagents for effecting this process include acetaldehyde, isobutyraldehyde, benzaldehyde, o-methylbenzaldehyde, m-methylbenzaldehyde, 3,4-dichlorobenzaldehyde, o-methoxybenzaldehyde o-chlorobenzaldehyde and cinnamaldehyde.

DETAILED DESCRIPTION OF THE INVENTION

The present process for the preparation of ascorbic acid utilizes as starting material a 1,4-lactone selected from gulono-1,4-lactone, galactono-1,4-lactone, idono-1,4-lactone and talono-1,4-lactone. These isomeric lactones differ in the stereochemistry of the hydroxyl groups at the 2- and 3-positions and may be represented by the formulae:

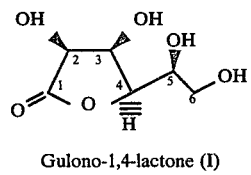

Gulono-1,4-lactone (I)

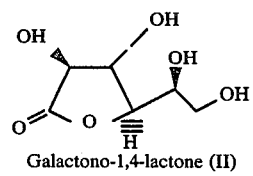

Galactono-1,4-lactone (II)

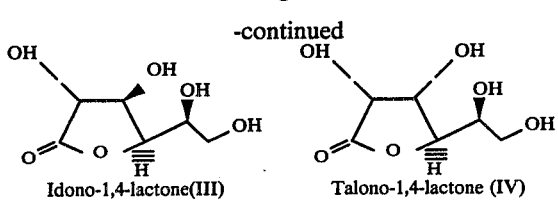

Idono-1,4-lactone(III)     Talono-1,4-lactone (IV)

and the enantiomers thereof.

The numbering of the lactone ring as used in the specification and claims herein is shown above in formula I.

The present process may be used to prepare either L-ascorbic acid or D-ascorbic, or mixtures of the two acids. L-ascorbic acid is derived from 1,4-lactones of the L-series, while D-ascorbic acid is prepared from the D-enantiomers. As used in the specification and claims hereof, reference to ascorbic acid, gulono-1,4-lactone, galactono-1,4-lactone, idono-1,4-lactone and talono-1,4-lactone and to intermediates derived therefrom is meant to include compounds of both the L-series and the D-series.

The lactone starting materials are well known in the art and can be obtained commercially or synthesized. For example, L-gulono-1,4-lactone can be prepared by the hydrogenation of D-glucuronolactone. L-galactono-1,4-lactone may be prepared from pectin via D-galacturonic acid. D-gulono-1,4-lactone can be prepared from D-xylose. See, for example, Chem. Pharm. Bull. 13, 173 (1965), Helv. Chim. Acta 21, 3 (1938); Bull Chem. Soc. Japan 13, 272 (1938); J.A.C.S. 49, 478 (1928); Helv. Chim. Acta 18, 482 (1938) and Organic Synthesis IV, 506 (1963). Gulono-1,4-lactone is a preferred starting material.

The first step in the present process is the formation of a protected intermediate, having an unprotected hydroxyl group remaining at either, but not both, the 2- or 3-position of the lactone ring. This may be effected in one embodiment of the invention by the reaction of the 1,4-lactone with about three equivalents of a hydroxyl-protecting reagent per mole of 1,4-lactone. As used in the specification and claims hereof, a hydroxyl-protecting reagent is considered to be any compound that will react with the hydroxyl groups of the lactone, replacing the hydrogen atom with a redical derived from the reagent, which radical can in subsequent steps be removed by hydrolysis to regenerate the hydroxyl groups. By an equivalent of hydroxyl-protecting reagent is meant the stoichiometric amount required to react with one hydroxyl group. The hydroxyl-protecting reagent may be monofunctional, by which is meant that one molecule of reagent reacts with one hydroxyl group of the lactone. When such a reagent is used the hydroxyl groups at the 5- and 6-positions and one of the hydroxyl groups at the 2- or 3-position will be protected. Since only three equivalents are employed only one of the hydroxyl groups at the 2- and 3-positions will react and a free hydroxyl group will remain at the other position. The protected intermediates formed by this reaction are of the formulae:

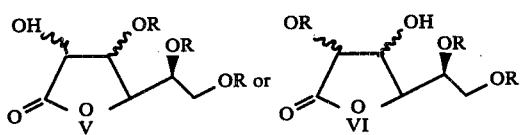

wherein R is a monofunctional hydroxyl-protecting group, as defined herein; or mixtures thereof, and their enantiomers.

Many monofunctional hydroxyl-protecting reagents are known in the art including, but not limited to, trialkylsilyl halides, wherein each alkyl is of 1 to 6 carbon atoms; alkanoyl halides of 2 to 6 carbon atoms; aroyl halides, wherein aroyl is benzoyl, naphthoyl or monosubstituted benzoyl, wherein said substituents are alkyl of 1 to 6 carbon atoms, alkoxy of 1 to 6 carbon atoms, halo or nitro, alkanoic anhydrides of 3 to 8 carbon atoms; alkyl vinyl ethers, wherein said alkyl is of 1 to 6 carbon atoms; alkyl mono- or di-substituted vinyl ethers, wherein said substituents are alkyl of 1 to 6 carbon atoms or halo; and triphenylmethyl halides. The choice of hydroxyl-protecting reagent is not critical and any compound which will allow formation of a protected intermediate which can be oxidized at the 2- or 3-position and the hydroxyl-protecting groups removed thereafter can be employed. A preferred class of monofunctional hydroxyl-protecting reagents is trialkylsilyl halides, wherein each alkyl is of 1 to 6 carbon atoms. Of these, trimethylsilyl halides and t-butyl-dimethylsilyl halides are especially preferred. Another preferred class of monofunctional reagents is alkanoic anhydrides of 3 to 8 carbon atoms; these are considered as monofunctional reagents for the purposes of this process, since the anhydride reacts dissociatively and each lactone hydroxyl reacted is esterified. A preferred alkanoic anhydride is acetic anhydride. Other preferred hydroxyl-protecting reagents are alkanoyl halides of 2 to 6 carbon atoms; especially preferred are acetyl chloride and acetyl bromide. A further preferred class of hydroxyl-protecting reagents is aroyl halides, wherein said aroyl is benzoyl, napthoyl or monosubstituted benzoyl, wherein said substituents are alkyl of 1 to 6 carbon atoms, alkoxy of 1 to 6 carbon atoms, halo or nitro. Especially preferred are benzoyl chloride and benzoyl bromide. A preferred triphenylmethyl halide is triphenylchloromethane.

In a further embodiment of this invention, difunctional hydroxyl-protecting reagents may be employed. By a difunctional hydroxyl-protecting reagent is meant a compound one molecule of which can react with two hydroxyl groups of the lactone to form a bridged intermediate. Thus, one mole of such a reagent provides two equivalents of hydroxyl-protecting reagent according to the definition used herein. The difunctional hydroxyl-protecting reagents may be effective to form two types of intermediates, depending on the choice of reagent employed. Difunctional reagents react to form a 5,6-bridged intermediate. Examples of difunctional hydroxyl-protecting reagents that can be employed in the formation of such an intermediate include, but are not limited to, dialkylsilyl halides, alkyl isocyanates, and alkyl haloformates, wherein each alkyl is of 1 to 6 carbon atoms; aryl isocyanates, wherein aryl is phenyl, monosubstituted or disubstituted phenyl, wherein the substituents are alkyl of 1 to 6 carbon atoms, alkoxy of 1 to 6 carbon atoms, halo or nitro; and alkyl aldehydes of 2 to 8 carbon atoms. Choice of reagent is not critical. When a difunctional hydroxyl-protecting reagent is employed it is preferably used in the amount of about two equivalents in conjunction with one equivalent of a monofunctional hydroxyl-protecting reagent, which reacts with one of the hydroxyl groups at the 2- or 3-position of the lactone, to form an intermediate of the type:

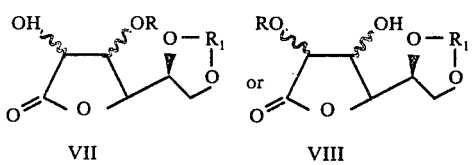

VII     VIII wherein $R_1$ is a difunctional hydroxyl-protecting group and R is a monofunctional hydroxyl-protecting group, as defined herein; or mixtures thereof, and their enantiomers.

A preferred class of difunctional hydroxyl-protecting reagents is dialkylsilyl halides, wherein each alkyl is of 1 to 6 carbon atoms. Another class of preferred hydroxyl-protecting reagents is dialkyl ketones, wherein each alkyl is of 1 to 6 carbon atoms, especially preferred are acetone, methyl ethyl ketone and methyl isobutyl ketone. A further class of preferred difunctional hydroxyl-protecting reagents is alkyl aldehydes of 2 to 8 carbon atoms; especially preferred compounds are acetaldehyde and propionaldehyde. The alkyl aldehydes may be used directly or in the form of their dialkyl acetals and reference to such aldehydes in the specification and claims hereof is intended to include such acetals.

Formation of the protected intermediates described above and represented by formulae V through VIII is generally conducted in non-hydroxylic organic solvents. Suitable solvents include, but are not limited to, dimethyl formamide, pyridine and dimethyl sulfoxide. It is not necessary, however, that the starting lactone be fully soluble in the organic medium and the protected intermediate can be prepared in a heterogeneous system where the lactone is dispersed in an inert organic diluent. The 1,4-lactone is contacted with the appropriate hydroxyl-protecting reagent at temperatures in the range of about $-10°$ C. to $150°$ C. Temperature is, however, not critical and usually the reaction can be most conveniently accomplished at room temperature. The hydroxyl-protecting reagent may be added to the solution of the 1,4-lactone either dropwise or in one batch. In either case, the mixture should be adequately stirred throughout the period of reaction. The time for complete reaction will, of course, vary with the temperature and concentration of reagents. In general, however, the reaction will be substantially complete in a period of about 30 minutes to about 15 hours. When alkyl aldehydes are employed in forming the protected intermediates described above, the reaction may be advantageously conducted in the presence of a weak Lewis acid catalyst, such as cupric sulfate or ferric chloride.

A limited number of difunctional hydroxyl-protecting reagents have been found to form a 3,5-adduct of the type:

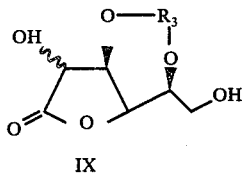

IX wherein $R_3$ is a difunctional hydroxyl-protecting group derived from an alkyl aldehyde, aryl aldehyde, arylalkyl aldehyde or arylalkenyl aldehyde, as defined hereinafter; and the enantiomer thereof. These 3,5-adducts are formed with such aldehyde hydroxyl-protecting reagents in the presence of a strong acid catalyst having a $pk_a$ of less than about 2.5.

Such intermediates are only formed with gulono-1,4-lactone and idono-1,4-lactone, in which the stereochemistry of the 3- and 5-hydroxyl groups allows the formation of this bridged compound. The hydroxyl-protecting reagents that have been found to form this type of intermediate are aryl aldehydes, arylalkyl aldehydes and arylalkenyl aldehydes, wherein aryl is phenyl, monosubstituted or disubstituted phenyl, wherein said substituents are alkyl of 1 to 6 carbon atoms, alkoxy of 1 to 6 carbon atoms, halo or nitro, and alkyl and alkenyl are each of 2 to 4 carbon atoms; and alkyl aldehydes of 2 to 8 carbon atoms. Preferred alkyl aldehydes are acetaldehyde and isobutyraldehyde. Preferred aryl aldehydes include benzaldehyde, o-methylbenzaldehyde, m-methylbenzaldehyde, 3,4-dichlorobenzaldehyde, o-methoxybenzaldehyde and o-chlorobenzaldehyde. Benzaldehyde is an especially preferred reagent. Another especially preferred reagent is o-methoxybenzaldehyde. A preferred arylalkenyl aldehyde is cinnamaldehyde.

Formation of the 3,5-protected intermediates described above and represented by formula IX is conducted in an organic solvent or diluent. Suitable solvents are non-hydroxylic organic compounds such as dimethylformamide, pyridine and dimethyl sulfoxide. A particularly preferred process employs an excess of the aldehyde hydroxyl-protecting reagent as solvent or diluent. Since the intermediate is a 3,5-adduct, further reaction of the aldehyde with other hydroxyl groups of the same lactone ring does not occur. Thus, for example, the 1,4-lactone can be contacted with from about 3 to about 10 equivalents of the aldehyde hydroxyl-protecting reagent. Two equivalents of the aldehyde hydroxyl-protecting reagent are consumed by reaction with the 1,4-lactone to form the 3,5-adduct, while the remainder acts as solvent or diluent. The formation of the 3,5-adduct requires the presence of a strong acid catalyst having a $pk_a$ of less than about 2.5, generally added in an amount between about 0.05 and about 1.5 moles per mole of 1,4-lactone. Suitable acid catalysts include, but are not limited to, hydrochloric acid, sulfuric acid, p-toluenesulfonic acid, sulfonic ion exchange resins and polyphosphoric acid. Temperatures between about $-10°$ C. and $150°$ C. may be employed. Temperatures are not critical, however, and the reaction is usually conducted at about room temperature. The hydroxyl-protecting reagent may be added to the solution of the 1,4-lactone either dropwise or in one batch while stirring the reaction mixture. The time for complete reaction will depend on the temperature and the concentration of the reagents. In general, however, the reaction will be substantially complete in a period of about 30 minutes to about 15 hours.

The 3,5-adducts of formula IX may also be formed from 5,6-adducts formed with alkyl aldehyde protecting groups by heating in the presence of a strong acid catalyst as described above.

The 3,5-adduct of formula IX can be used directly in the next step of the process i.e., the oxidation of the hydroxyl group to a keto group. The free hydroxyl at the 2-position may be selectively oxidized in preference to the other free hydroxyl at the 6-position of the lactone. Thus, in this embodiment of the present invention, the first step in the process may be effected by contacting a 1,4-lactone selected from gulonolactone and idonolactone in the presence of an acid catalyst having a $pk_a$ of less than about 2.5 with at least about two equivalents of a hydroxyl-protecting reagent per mole of 1,4-lactone, said reagent being selected from an alkyl aldehyde of 2 to 8 carbon atoms; an aryl aldehyde, an arylalkyl aldehyde and an arylalkenyl aldehyde, wherein said aryl is phenyl, monosubstituted or disubstituted phenyl wherein said substituents are alkyl of 1 to 6 carbon atoms, alkoxy of 1 to 6 carbon atoms halo or nitro, and said alkyl and alkenyl are each of 2 to 4 carbon atoms. This is a preferred embodiment of the present process.

The above reactions can also be employed to form intermediates of the formula:

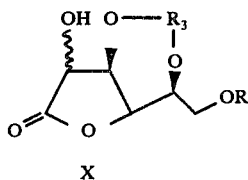

X wherein R is a monofunctional hydroxyl-protecting group and $R_3$ is a difunctional hydroxyl-protecting group derived from an alkyl aldehyde, an aryl aldehyde, an arylalkyl aldehyde or an arylalkenyl aldehyde, as defined above; and the enantiomer thereof.

A preferred monofunctional hydroxyl-protecting reagent for the formation of therse intermediates is a triphenylmethyl halide, such as triphenylchloromethane. Intermediates of formula X are suitable for oxidation of the 2-hydroxyl group to a keto group in the same way as other 3,5-adducts, as described hereinafter.

In specifying the amount of hydroxyl-protecting reagent required to form the above protected intermediates, i.e., about three equivalents or about two equivalents per mole of 1,4-lactone, depending on the hydroxyl-protecting reagent employed, it will of course be recognized that lesser amounts of reagent can be used with corresponding lower yields of the intermediate. It is intended that the specification and claims hereof include a process where only a part of the 1,4-lactone starting material is reacted and unreacted 1,4-lactone may be subsequently recycled for further reaction. It is, of course, advantageous to avoid such recycle and the present process allows high yields in a single pass.

The protected intermediates formed in the first step of the process as described above, may be used directly in the next step of the present process without further purification. If desired, however, the protected intermediates may be isolated and purified by recrystallization or other means known in the art. Preferably, before use in the next step excess solvent is removed.

The second step in the present process is the oxidation of the unprotected hydroxyl group, located at the 2- or 3-position of the protected lactone, to keto. This may be effected by methods known in the art for the oxidation of secondary alcohols to ketones. However, choice of oxidizing agents will be affected by the protecting groups employed and the type of intermediate formed in the first step of the process. For example, oxidation of the 3,5-protected intermediates and others having a free hydroxyl group at the 2-position of the lactone may conveniently be effected with manganese dioxide. In the case of the 3,5-intermediates having a free hydroxyl group at the 6-position of the lactone, as shown in formula IX, the hydroxyl group at the 2-position is oxidized preferentially by such use of manganese dioxide. Any of the intermediates formed in the first step of the process may be oxidized via a sulfoxonium salt, formed from a mixture of dimethyl sulfoxide and, for example, acetic anhydride or trifluoroacetic anhydride, or from a mixture of dimethylsulfide and N-chlorsuccinimide, in the presence of a base, such as triethylamine. Oxidation may also be effected catalytically using either pure oxygen or an oxygen-containing gas. A suitable catalyst is platinum. Oxidation may also be effected electrochemically. The oxidation is conducted in an organic solvent, which may be the same as that used in the first step of the process in forming the protected intermediate. However, other solvents may be used and in general, any organic solvent inert to oxidation conditions can be employed. Examples of suitable solvents include, but are not limited to, dimethyl formamide, pyridine, dimethyl sulfoxide, dichloromethane and acetone. It is not necessary that the intermediate be fully soluble in the organic medium. Temperatures suitable for the oxidation reaction will vary according to the type of oxidation employed. For example, in oxidation via sulfoxonium salts, the oxidation may be conducted at about $-60°$ C. to $100°$ C. depending on the method used to generate the initial sulfonium salt. The reaction is preferably conducted at about $0°$ C. to $50°$ C. Oxidation by manganese dioxide is conducted at about $-10°$ C. to about $75°$ C., preferably about $0°$ C. to room temperature. Catalytic oxidation using platinum and oxygen may be conducted at about room temperature to about $100°$ C., preferably about $50°$ C. to about $75°$ C. Before proceeding to the next step of the process the oxidized intermediate should be separated from any excess oxidizing agent, for example, by filtration of solid catalyst residues of by extraction or recrystallization of the product. If desired, the oxidized intermediate can be isolated and purified by means known in the art; however, this is not necessary. The oxidized intermediates may exist in the keto, enol or hydrated forms depending on the protecting groups employed. The 3,5-protected intermediates are generally isolated as the hydrated or keto form.

The oxidized intermediates formed as described above are novel compounds. Particularly useful and preferred intermediates are those of the formula

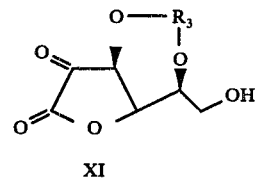

XI and the hydrated form thereof, wherein $R_3$ is a hydroxyl-protecting group derived from an alkyl aldehyde of 2 to 8 carbon atoms; an aryl aldehyde, an arylalkyl aldehyde or an arylalkenyl aldehyde, wherein said aryl is phenyl, mono-substituted or di-substituted phenyl, wherein said substituents are alkyl of 1 to 6 carbon atoms, alkoxy of 1 to 6 carbon atoms, halo or nitro, and said alkyl and alkenyl are each of 2 to 4 carbon atoms. These are formed by oxidation of compounds of formula IX as described above.

The final step in the present process is the removal of the hydroxyl-protecting groups by hydrolysis and subsequent rearrangement to yield ascorbic acid. Hydrolysis may generally be effected under said acid conditions.

Suitable acids for effecting removal of the hydroxyl-protecting groups include hydrochloric acid, sulfuric acid, acetic acid and other lower alkyl carboxylic acids and sulfonic ion exchange resins. Hydrolysis may be conducted in aqueous organic co-solvent mixtures, with methanol and other lower alkyl alcohols being suitable solvents. Another preferred hydrolysis medium is aqueous acetic acid. With some hydroxyl-protecting groups hydrolysis may also be effected under basic conditions, for example, where ester intermediates are employed. Suitable bases include sodium carbonate, sodium hydroxide and similar salts. The ascorbic acid is then obtained in the form of the sodium or other metal salt and can be converted to the free acid by treatment with a dilute acid, such as hydrochloric acid, or by ion exchange. Under either basic or acidic hydrolysis conditions temperatures are not critical, generally temperatures in the range of about 35° C. to 100° C. being suitable with temperatures of about 50° C. to 75° C. being preferred. Under some strong acid or basic hydrolysis conditions the lactone ring may be opened to form methyl 2-ketogulonate or 2-ketogulonic acid. These can be readily converted by further reaction to ascorbic acid by means known in the art and thus the formation of these intermediates is not detrimental to the present process. If desired, the methyl 2-ketogulonate or 2-ketogulonic acid may be isolated and purified. The ascorbic acid produced can be purified by means known in the art, for example by recrystallization from methanol, methanol-water or other suitable solvents or solvent mixtures.

The process of the present invention is further illustrated by the following examples. It should be understood, however, that the invention is not limited to the specific details of these examples.

EXAMPLE 1

To 50 ml of dry DMF was added 8.91 g (50 mmol) of L-gulono-1,4-lactone. To this homogeneous solution was added 24.04 g (395 mmol) of imidazole and 23.27 g (156 mmol) of t-butyldimethylchlorosilane. The reaction was slightly exothermic initially and was stirred under nitrogen for 15 hours. At that time 350 ml of benzene was added and this solution was extracted 5 times with 50 ml of water, 2 times with brine, and then it was dried with anhydrous sodium sulfate. Removal of the solvent under vacuum afforded 26.3 g (50.5 mmol, 100%) of a colorless oil which tlc revealed contained two components. This material was chromatographed on 510 g of silica gel using 0.25% methanol-benzene to elute the faster moving component (16.2 g, 31.1 mmol, 62.2%) and then using 0.5% methanol-chloroform to 2% methanol-chloroform to elute the slower moving component (8.2 g, 15.9 mmol, 31.9%).

The faster moving component was shown to be 2,5,6-tri-O-t-butyldimethylsilyl-L-gulono-1,4-lactone by nmr decoupling experiments. An analytically pure sample was prepared by preparative gas chromatography on 10% SE 30 on A/W DMCS Chromosorb G: ir (neat) 3550, 1800 cm$^{-1}$; nmr (DMSO-d$_6$) $\delta_H$ 0.08 (m, 18), 0.90 (m, 27), 3.57–4.40 (m, 5), 4.63 (d, 1, J = 4, —CHCO$_2$—), 5.12 (d, 1, J = 4, —OH); in benzene three different t-butyl groups can clearly be seen in the nmr.

Analytical: Calcd. for C$_{24}$H$_{52}$O$_6$Si$_3$: C, 55.33; H, 10.06. Found: C, 55.17; H, 9.79.

The slower moving component was shown to be 3,5,6-Tri-O-t-butyldimethylsilyl-L-gulono-1,4-lactone by nmr decoupling experiments. An analytically pure sample was prepared by preparative gas chromatography on 10% SE 30 an A/W DMCS Chromosorb G: ir (neat) 3400, 1790 cm$^{-1}$; nmr (DMSO-d$_6$) $\delta_H$ 0.10 (m, 18), 0.93 (m, 27), 3.50–4.67 (m, 6), 6.03 (d, 1, —OH).

Analytical: Calcd for C$_{24}$H$_{52}$O$_6$Si$_3$: C, 55.33; H, 10.06. Found: C, 55.41; H, 9.93.

EXAMPLE 2

To 120 ml of dry dichloromethane under nitrogen was added 4.2 ml (59 mmol) of dimethylsulfoxide. This solution was cooled to less than −55° and 8.0 ml (56.5 mmol) of trifluoroacetic anhydride was added. The resulting heterogeneous solution was stirred for 30 min below −50°. Then 15.0 g (28.1 mmol) of a mixture of 2,5,6-tri-O-t-butyldimethylsilyl-L-gulono-1,4-lactone and 3,5,6-tri-O-t-butyldimethylsilyl-L-gulono-1,4-lactone in 50 ml of dry dichloromethane was added to the reaction mixture. The temperature during the addition was maintained below −55°. The reaction mixture was stirred at less than −55° for 30 min at which time 12 ml (86 mmol) of dry triethylamine was added. After stirring at −60° or below for 30 min, the reaction mixture was allowed to warm to room temperature and stirred for 3 hours. The reaction was worked up by extracting with water, 1N hydrochloric acid, water, and then brine and finally drying with anhydrous sodium sulfate. Removal of the solvent afforded 12.6 g of material. To this material was added 50 ml of THF, 20 ml of water, and 50 ml of glacial acetic acid. This solution was heated at 75° for 24 hours and the solvent was then removed under vacuum. The resulting dark semi-solid (4.8 g) contained ascorbic acid which was identical to authentic ascorbic acid by glpc and tlc. By iodine titration the yield of ascorbic acid from the mixture of triprotected derivatives of L-gulono-1,4-lactone was 31%.

EXAMPLE 3

To a dry flank under nitrogen containing 5 ml of dry dichloromethane was added 0.293 g (1.4 mmol) of trifluoroacetic anhydride. After cooling to −60°, 0.10 ml (1.4 mmol) of dry DMSO was added. After 30 min, 0.618 g (1.2 mmol) of 2,5,6-tri-O-t-butyldimethylsilyl-L-gulono-1,4-lactone in 2 ml of dry dichloromethane was added. The reaction mixture was stirred at less than −50° for 30 min and then warmed to room temperature. When the temperature reached 10°, 0.2 ml (14.4 mmol) of triethylamine was added. After 45 min, 60 ml of dichloromethane was added. This solution was extracted with 1N hydrochloric acid, water, and brine and then dried with sodium sulfate. Removal of the solvent afforded 0.533 g (1.03 mmol), 86%) of a clear semi-solid material whose ir and nmr were consistent with those expected for 2,5,6-Tri-O-t-butyldimethylsilyl-L ascorbic acid. This product may be hydrolyzed to L-ascorbic acid by the procedure of Example 2.

EXAMPLE 4

3,5,6-Tri-O-t-butyldimethylsilyl-L-gulono-1,4-lactone was oxidized by a procedure identical to that described in Example 3 for the preparation of 2,5,6-tri-O-t-butyldimethylsilyl-L-ascorbic acid. From 0.53 g (1.02 mmol) of 3,5,6-tri-O-t-butyldimethylsilyl-L-gulono-1,4-lactone was obtained a slightly yellow oil containing 3,5,6-tri-O-t-butyldimethylsilyl-L-ascorbic acid. This may be hydrolyzed to L-ascorbic acid by the procedure of Example 2.

EXAMPLE 5

To a dry 500-ml 3-neck flask fitted with a mechanical stirrer was added 68 ml (0.67 mol) of benzaldehyde. Hydrogen chloride gas was bubbled through the benzaldehyde for one minute and then 30.0 g (0.169 mol) of L-gulono-1,4-lactone was added to the solution. The reaction mixture was stirred for several minutes and then 0.3 g of seed crystals of 3,5-O-benzylidene-L-gulono-1,4-lactone was added. (Seed crystals are obtained by prior reactions run without the addition of such crystals. Addition of seed crystals is not necessary but results in better yields). After approximately 1.5 hours, the reaction mixture became very thick and stirring was stopped. After standing overnight, the reaction mixture was triturated with ether and filtered. The solid was washed thoroughly with ether 3 times, with water 3 times, and then with ether an additional 2 times. After drying this afforded 33.3 g (0.125 mol, 74%) of 3,5-O-benzylidene-L-gulono-1,4-lactone. Recrystallization from absolute ethanol afforded pure material in 65% yield, mp 188°-189°: $[\alpha]_D^{23}$ + 61.1 (DMF); ir (KBr) 3472, 3279, 1788 cm$^{-1}$; nmr (DMSO-d$_6$) $\delta_H$ 3.43 (broad t, 2, —CH$_2$O—), 4.0–4.83 (m,4), 4.97 (t, 1, J = 5, —CH$_2$OH), 5.68 (s, 1, —OCHO—), 5.97 (m, 1, —CHOH), 7.4 (m, 5, aromatic); nmr (DMSO-d$_6$) $\delta_C$ 175.9 (s, 1, —CO$_2$—), 137.7 (s, 1, aromatic), 129.0, 128.1, and 126.5 (s, aromatic), 98.2 (d, 1 —OCHO—), 76.2, 74.8, 70.8, 69.5 (4), 59.9 (t, 1, —CH$_2$OH); ms 266 (27.2), 265 (20.2), 235 (24.5), 160 (30.1), 107 (90.2), 105 (100), 79 (50.8), 77 (51.5), and 57 (21.1).

This compound was also prepared by the above procedure but employing one equivalent of concentrated hydrochloric acid as the acid catalyst.

To 70 ml of acetone was added 5.32 g (20 mmol) of 3,5-O-benzylidene-L-gulono-1,4-lactone followed by 21.2 g (0.246 mmol) of manganese (IV) oxide. The reaction mixture was stirred at room temperature for 3 hours. After filtering the solvent was removed under vacuum to afford 4.42 g (15.7 mmol, 78%) of 3,5-O-benzylidene-L-xylo-hexulosono-1,4-lactone hydrate as a white amorphous solid which was analytically pure. This white solid was shown to be the hydrated form of the xylo-hexulosono-1,4-lactone by the ir, $^1$H-nmr, and $^{13}$C-nmr: ir (KBr) 3472, 1812 cm$^{-1}$; nmr (DMSO-d$_6$) $\delta_H$ 3.67 (broad t, 2, —CH$_2$O—), 4.08–4.65 (m, 3), 5.02 (t, 1, J = 5, —CH$_2$OH), 5.75 (s, 1, —OCHO—), 7.15 (s, 1, —OH), 7.52 (s, 6, aromatic and —OH); nmr (DMSO-d$_6$) $\delta_C$ 179.9 (—CO$_2$—), 134.4, 129.1, 128.4, and 126.4 (aromatic), 98.1 and 97.2 (—OCHO— and —CH(OH)$_2$), 93.8 (—OCH—C(OH)$_2$), 76.2 and 70.8 (—OCH—), 60.0 (—CH$_2$OH); exact mass (C$_{13}$H$_{12}$O$_6$), 264.0637 (calc 264.0640).

Analytical: Calcd for C$_{13}$H$_{12}$O$_6$·H$_2$O: C, 55.32; H, 5.00. Found: C, 55.05; H, 5.02.

To 50 ml of 70% acetic acid—water under nitrogen was added 6.362 g (22.6 mmol) of 3,5-O-benzylidene-L-xylo-hexulosono-1,4-lactone. The heterogeneous reaction was heated to 70°–75° and after 1 hr it was homogeneous. After 4 hr the reaction was worked up by removing the solvent in vacuo. To the residual solid was added 25 ml of chloroform and 25 ml of water. The layers were separated, the chloroform layer was washed with 10 ml of water, and the water layers were combined and concentrated in vacuo affording 3.796 g (21.5 mmol) of an off-white solid. Iodine titration of 0.222 g of this material showed the yield of ascorbic acid to be 70%. Recrystallization of the remaining solid from methanol—ethyl acetate afforded 0.550 g of ascorbic acid in the first crop, 1.399 g in the second crop, and 0.247 g in the third crop for a total of 2.196 g (12.5 mmol, 59%). This material was identical with authentic ascorbic acid by tlc, glpc, ir, and nmr, mp 184°-5° (authentic 185°-6°): ir (KBr) 3497, 3378, 3268, 3165, 2976, 2688, 1751, 1653 cm$^{-1}$, nmr (D$_2$O) $\delta_H$ 3.7–4.3 (m, 3), 4.75 (s, —OH), 5.02 (d, 1, J = 2, ring —CH).

EXAMPLE 6

To a solution of 38 ml of acetone and 7 ml of water was added 2.39 g (9.0 mmol) of 3,5-O-benzylidene-L-gulono-1,4-lactone and 0.65 g of platinum oxide. The reaction was carried out in a resin flask and rapidly agitated with a Vibro mixer. Oxygen was bubbled through the solution at a rapid rate. The initial pH of the solution was 7.4 but it rapidly dropped to 4.3 and remained there during the 7 hr oxygen was passed through the solution. At the end of that period, the catalyst was removed by filtration and the solvent was removed under vacuum. The resulting solid was chromatographed on 100 g of silica gel with ethyl acetate—chloroform—methanol (60:40:1). From the column was obtained 0.240 g (0.85 mmol, 9.5%) of 3,5-O-benzylidene-L-xylo-hexulosono-1,4-lactone hydrate. This material was identical with that which had been previously obtained by oxidation with manganese dioxide. The product may be converted to L-ascorbic acid by the procedure of Example 5.

EXAMPLE 7

To 2 ml of methanol and 1 ml of water was added 0.221 g (0.78 mmol) of 3,5-O-benzylidene-L-xylo-hexulosono-1,4-lactone hydrate followed by 0.16 g if IR-120 cation exchange resin. After stirring the reaction mixture at room temperature for 0.5 hours, it was warmed to 50°. After 1.25 hours, an additional 0.16 g of IR-120 cation exchange resin was added. The reaction was stirred overnight. The cation exchange resin was then filtered off, washed with water, and then the aqueous solution was extracted with chloroform. On removal of the solvent, 0.138 g of an off-white solid was isolated. The yield of ascorbic acid was 61% (determined by hplc).

EXAMPLE 8

3.0 g (10.6 mmol) of 3,5-O-benzylidene-L-xylo-hexulosono-1,4-lactone hydrate was added to 45 ml of 33% water-methanol solution followed by 2.12 g of IR-120 cation exchange resin. The reaction mixture was heated at 50° for 16 hours and at 60° for 4 hours. The reaction mixture was then filtered, washed with chloroform, and concentrated to a viscous oil which was triturated with ethanol to afford 1.42 g of a white solid. A portion of this material was purified by chromatography on IR-45 weakly basic ion exchange resin. The column was initially eluted with water to elute non-acidic impurities and then with 0.5N HCl to elute the L-ascorbic acid. After removing the water, the resulting solid was triturated with chloroform-ethanol and recrystallized from methanol. The ir and nmr spectra of this material were identical with authentic ascorbic acid.

EXAMPLE 9

Through 25 ml of dry methanol was bubbled anhydrous hydrogen chloride for approximately 30 seconds.

To this solution was added 2.60 g (12.8 mmol) of 3,5-O-benzylidene-L-xylo-hexulosono-1,4-lactone hydrate. The reaction mixture was heated to 50° for 1 hour at which time the solvent was removed. The resulting solid was dissolved in water and this was extracted with ether. The ether layer was extracted with water and the combined aqueous fractions were concentrated to a tacky foam. By hplc this material was essentially pure methyl 2-keto-L-gulonate. Recrystallization from methanol afforded 0.602 g (2.80 mmol, 23%) of pure methyl 2-ketogulonate, mp 158°–162°. The nmr and ir spectra were identical with authentic methyl 2-keto-L-gulonate. The mixed mp of authentic material (157°–160°) with the material isolated above was 158 –162°. The methyl 2-ketogulonate may be converted to L-ascorbic acid by heating in solution in the presence of an acid or base catalyst.

EXAMPLE 10

To a dry flask was added 1.78 g (10 mmol) of L-gulono-1,4-lactone, 4.83 ml (40 mmol) of 2-methoxybenzaldehyde, and 0.8 ml (9.7 mmol) of concentrated hydrochloric acid. After standing at room temperature overnight, the solid reaction mixture was worked up by washing with ether, water, and then ether. This afforded 2.70 g (9.1 mmol, 91%) of 3,5-O-(2-methoxybenzylidene)-L-gulono-1,4-lactone. Analytically pure material was obtained by recrystallization from acetonitrile, mp 220°–221°: $[\alpha]_D^{23}$ + 64.2 (DMF); ir 3521, 3311, 1802 cm$^{-1}$; nmr (DMSO-d$_6$) $\delta_H$ 3.62 (m, 2, —CH$_2$O—), 3.83 (s, 3, —OCH$_3$), 4.03–4.83 (m, 4), 4.96 (t, 1, J = 6, —CH$_2$OH), 5.95 (s and m, 2, —OCHO— and —OH), 6.83–7.64 (m, 4, aromatic); ms 296 (40.7), 265 (38.8), 160 (48.1), 137 (86.0), 136 (44.9), 135 (100), 121 (27.0), 119 (21.4), 107 (49.9), and 77 (25.5).

Analytical: Calcd for C$_{14}$H$_{16}$O$_7$: C, 56.75; H, 5.44. Found: C, 56.92; H, 5.50.

Following the procedure of Example 5, from 1.18 g (4 mmol) of 3,5-O-(2-methoxybenzylidene)-L-gulono-1,4-lactone was isolated 0.710 g (2.27 mmol, 57%) of 3,5-O-(2-methoxybenzylidene)-L-xylo-hexulosono-1,4-lactone hydrate as a white amorphous solid: ir (KBr) 3333, 1770 cm$^{-1}$; nmr (DMSO-d$_6$) $\delta_H$ 3.47–4.83 (m, 5), 3.83 (s, 3, —OCH$_3$), 5.0 (t, 1, J = 5, —CH$_2$OH), 6.0 (s, 1, —OCHO—), 6.83–7.63 (m, 6, aromatic and —OH); exact mass (C$_{14}$H$_{14}$O$_7$) 294.0725 (calcd 294.0711).

Analytical: Calcd for C$_{14}$H$_{14}$O$_7$.0.5 H$_2$O: C, 55.44; H, 4.98. Found: C, 55.30, H, 5.29.

To 5.2 ml of 70% acetic acid - water was added 0.523 g (1.7 mmol) of 3,5-O-(2-methoxybenzylidene)-L-xylo-hexulosono-1,4-lactone hydrate. This heterogeneous solution was at 70° for 2 hours. The reaction mixture was transferred to a separatory funnel with water and extracted 2 times with dichloromethane. The aqueous solution was concentrated under vacuum and afforded a white foam, 0.397 g. This material was dissolved in deuterium oxide to which was added acetonitrile as an internal nmr standard. The nmr spectrum of an aliquot of this material indicated that L-ascorbic acid had been formed in 49% yield.

EXAMPLE 11

L-gulono-1,4-lactone (1.78 g, 10 mmol), 2-methylbenzaldehyde (3.1 ml, 40 mmol), and concentrated hydrochloric acid (0.81 ml, 9.7 mmol) were combined. After 0.75 hours the reaction mixture turned solid and after standing overnight the reaction was worked up as previously described in Example 5 to afford 2.32 g (8.3 mmol, 83%) of 3,5-O-(2-methylbenzylidene)-L-gulono-1,4-lactone. Analytically pure material was obtained by recrystallization from acetonitrile, mp 208°–210°: $[\alpha]_D^{23}$ + 64.6 (DMF); ir (KBr) 3240, 1786 cm$^{-1}$; nmr (DMSO-d$_6$) $\delta_H$ 2.36 (s, 3, —CH$_3$), 3.5–4.83 (m, 6), 5.0 (m, 1, —CH$_2$OH), 5.86 (s, 1, —OCHO—), 6.0 (m, 1, —OH), 7.13–7.66 (m, 4, aromatic); ms 280 (53.1), 121 (64.3), 120 (58.1), 119 (100), 93 (38.1), and 91 (60.7).

Analytical: Calcd for C$_{14}$H$_{16}$O$_6$: C, 59.99; H, 5.75. Found: C, 60.18; H, 5.75.

Following the procedure of Example 5, 1.4 g (5 mmol) of 3,5-O-(2-methylbenzylidene)-L-gulono-1,4-lactone was converted to 1.12 g (3.78 mmol, 76%) of 3,5-O-(2-methylbenzylidene-L-xylo-hexulosono-1,4-lactone hydrate as a white amorphous solid: ir (KBr) 3378, 1792 cm$^{-1}$; nmr (DMSO-d$_6$) $\delta_H$ 2.38 (s, 3, —CH$_3$), 3.25–4.75 (m, 5), 5.83 (d, 1, —OCHO—), 7.33 (m, 4, aromatic); ms 279 (10.1), 278 (77.5), 163 (40.2), 121 (100), 120 (32.3), 119 (66.2), 105 (87.8), 93 (36.8), 91 (71.3); exact mass (C$_{14}$H$_{14}$O$_6$), 278.0802 (calcd 278.0812).

The product may be converted to ascorbic acid by hydrolysis by the procedure of Example 5.

EXAMPLE 12

3,4-dichlorobenzaldehyde (14.0 g, 80 mmol), L-gulono-1,4-lactone (3.56 g, 20 mmol), and 1.62 ml (19.5 mmol) of concentrated hydrochloric acid were combined. After 0.5 hours the reaction mixture turned solid. After standing overnight at room temperature, the reaction was worked up as previously described to afford 6.70 g (20 mmol, 100%) of 3,5-O-(3,4-dichlorobenzylidene)-L-gulono-1,4-lactone. Analytically pure material was obtained by recrystallization from ethyl acetate-acetonitrile, mp 230°–232°: $[\alpha]_D^{23}$ + 37.2 (DMF); ir (KBr) 3367, 1780 cm$^{-1}$; nmr (DMSO-d$_6$) $\delta_H$ 3.66 (m, 2, —CH$_2$—), 4.0–4.86 (m, 4), 5.01 (t, 1, J = 6, —CH$_2$OH), 5.76 (s, 1, —OCHO—), 5.93–6.2 (m, 1, —OH), 7.3–7.8 (m, 3, aromatic); ms 335 (3.1), 333 (6.8), 177 (21.3), 175 (55.3), 173 (35.7), 111 (21.9), 85 (46.3), 71 (42.3), 69 (28.9), 57 (100), and 55 (30.2).

Analytical: Calcd for C$_{13}$H$_{12}$O$_6$Cl$_2$: C, 46.58; H, 3.61. Found: C, 46.46; H, 3.64.

Following the procedure of Example 5, from 2.01 g (6 mmol) of 3,5-O-(3,4-dichlorobenzylidene)-L-gulonolactone was isolated 1.28 g (3.64 mmol, 61%) of 3,5-O-(3,4-dichlorobenzlidene)-L-xylo-hexulosono-1,4-lactone hydrate as a white amorphous solid: ir (KBr) 3333, 1792 cm$^{-1}$; nmr (DMSO-d$_6$) $\delta_H$ 3.55–4.70 (m, 5), 5.05 (t, 1, J = 5, —CH$_2$OH), 5.8 (s, 1, —OCHO—), 7.2 (s, 1, —OH), 7.37–7.97 (m, 4, aromatic and —OH); ms 334 (6.7), 332 (9.9), 177 (52.5), 175 (100), 173 (38.2), 147 (21.8), 113 (26.8), 111 (29.2), 85 (37.6), 84 (31.3), 75 (20.8), 74 (29.0), 57 (20.9) 56 (22.5), and 55 (27.0); exact mass (C$_{13}$H$_{10}$O$_6$Cl$_2$), 331.9860 (calcd 331.9866).

Analytical: Calcd for C$_{13}$H$_{10}$O$_6$Cl$_2$.0.25 H$_2$O: C, 46.24; H, 3.13. Found: C, 46.50; H, 3.58.

This product may be converted to L-ascorbic acid by the procedure of Example 5.

EXAMPLE 13

L-gulono-1,4-lactone (1.78 g, 10 mmol), 2-methylpropionaldehyde (3.68 ml, 40 mmol), and concentrated hydrochloric acid (0.81 ml, 9.7 mmol) were combined and stirred for 48 hours. The excess 2-methylpropionaldehyde was removed under vacuum. The resulting thick oil was triturated with ether and the resulting solid was collected to give 0.55 g, 24% of 3,5-O-(2- methylpropylidene)-L-gulono-1,4-lactone. Analytically pure material was obtained by recrystallization from ethyl acetate, mp 165°–167°: $[\alpha]_D^{23}$ + 77.4 (DMF); ir (KBr) 3333, 1786 cm$^{-1}$; nmr (DMSO-d$_6$) $\delta_H$ 0.85 (d, 6, J = 7, —CH$_3$), 1.67 (m, 1, —CH(CH$_3$)$_2$), 3.36–4.7 (m, 7), 4.83 (t, 1, J = 5, —CH$_2$OH), 5.76 (d, 1, J = 7, —O—CHO—); nmr (DMSO-d$_6$) $\delta_C$ 175.9 (s, —CO$_2$—), 102.4 (d, —OCHO—), 75.7, 74.2, 70.8, 69.6 (all d), 59.8 (t, —CH$_2$—), 32.2 (d, —CH(CH$_3$)$_2$), 17.0 (q, —CH$_3$); ms 231 (4.9), 189 (70.1), 160 (28.1), 125 (72.6), 113 (23), 97 (21.2), 85 (38.9), 83 (22.7), 73 (100), 72 (20.5), 71 (46.7), 69 (30.2), 57 (45.9), and 55 (46.9).

Analytical: Calcd for C$_{10}$H$_{16}$O$_6$: C, 51.71; H, 6.94. Found: C, 51.81; H, 6.94.

Following the procedure of Example 5, from 0.696 g (3 mmol) of 3,5-O-(2-methylpropylidene)-L-gulono-1,4-lactone was obtained 0.537 g (2.17 mmol, 72%) of 3,5-O-(2-methylpropylidene)-L-xylo-hexuloxono-1,4-lactone hydrate as a white amorphous solid, mp 179°–183° (dec): ir (KBr) 3378, 1779 cm$^{-1}$; nmr (DMSO-d$_6$) $\delta_H$ 0.90 (d, 6, J = 6, —CH$_3$), 1.67 (m, 1, —CH(CH$_3$)$_2$), 3.47–4.73 (m, 6), 4.91 (t, J = 5, —CH$_2$OH); ms 230 (4.8), 187 (58.2), 127 (23.8), 97 (20.3), 85 (38.8), 73 (52.2), 71 (23.2), 69 (29.8), 68 (20.3), 57 (53.1), 55 (64.3), 45 (28.3), 44 (39.9), 43 (100), and 41 (62.4); exact mass (C$_{10}$H$_{14}$O$_6$) 230.0787 (calcd 230.0783).

Analytical: Calcd for C$_{10}$H$_{14}$O$_6$·0.5 H$_2$O: C, 51.16; H, 6.22. Found: C, 51.13; H, 6.34.

3,5-O-(2-Methylpropylidene)-L-xylo-hexulosono-1,4-lactone hydrate was also prepared as follows. To a mixture of 30 ml of dioxane and 4 ml of water was added 0.60 g (2.59 mmol) of 3,5-O-(2-methylpropylidine)-L-gulono-1,4-lactone followed by 0.64 g of prereduced platinum oxide. The reaction mixture was heated to 70° and oxygen was bubbled through the solution. After 1 hour most of the starting material was gone, the catalyst was removed by filtration, and the solution concentrated in vacuo. Tlc and nmr confirmed the presence of 3,5-O-(2-methylpropylidene)-L-xylo-hexulosono-1,4-lactone.

The product may be converted to L-ascorbic acid by the procedure of Example 5.

EXAMPLE 14

To a dry 50-ml flask was added 3.56 g (20 mmol) of L-gulono-1,4-lactone, 9.0 ml (80 mmol) of 2-chlorobenzaldehyde, and 1.6 ml (19.2 mmol) of concentrated hydrochloric acid. The reaction mixture turned solid within 0.5 hours and after standing at room temperature overnight was worked up by washing with ether, saturated sodium bicarbonate, water, and ether. This afforded 4.78 g (15.9 mmol, 80%) of 3,5-O-(2-chlorobenzylidene)-L-gulono-1,4-lactone which was pure by tlc. Analytically pure material was obtained by recrystallization from acetonitrile, mp 208°–11°: $[\alpha]_D^{23}$ + 63.6 (DMF); ir (KBr) 3340, 1770 cm$^{-1}$; nmr (DMSO-d$_6$) $\delta_H$ 3.5–4.9 (m, 6), 5.03 (t, 1, J = 5, —CH$_2$OH), 5.93–6.16 (m, 1, —OH), 6.03 (s, 1, —OCHO—), 7.3–7.9 (m, 4, aromatic); ms 300 (1.4), 160 (39.6), 141 (64.3), 139 (27.3), 97 (22.3), 85 (52.7), 83 (27.2), 77 (34.8), 71 (57.8), 70 (20), 69 (35.3), 57 (100), and 55 (34.9).

Analytical: Calcd for C$_{13}$H$_{13}$O$_6$Cl: C, 51.92, h, 4.35. Found: C, 51.84; H, 4.32.

This product may be converted to L-ascorbic acid by the procedure of Example 5.

EXAMPLE 15

To 9.4 ml (80 mmol) of 3-methylbenzaldehyde was added 3.56 g (20 mmol) of L-gulono-1,4-lactone. After stirring for several minutes, 1.62 ml (19.4 mmol) of concentrated hydrochloric acid was added. On stirring at room temperature for 20 hr the initially mobile slurry had turned solid. The reaction mixture was triturated with ether, filtered, washed three times with ether, one time with water, two times with saturated sodium bicarbonate, two times with water, and finally one time with ether. The white solid after drying weighed 2.91 g (10.4 mmol, 52%), mp 188°–191° which was pure by tlc. Analytically pure 3,5-O-(3-methylbenzylidene)-L-gulono-1,4-lactone was obtained by recrystallization from acetonitrile, mp 198°–200°: $[\alpha]_D^{23}$ + 59.7° (DMF); ir (KBr) 3340, 3120, 1800 cm$^{-1}$; nmr (DMSO-d$_6$) $\delta_H$ 2.36 (s, 3, —CH$_3$), 3.50–3.83 (m, 2, —CH$_2$O—), 4.00–4.86 (m, 4), 5.00 (t, 1, J = 6, —CH$_2$OH), 5.73 (s, 1, —OCHO—), 5.98 (m, 1, —CHOH), 7.30 (s, 4, aromatic); ms 280 (9.0), 121 (38.4), 120 (26.7), 119 (100), 105 (16.1), 93 (45.8), 91 (59.7), 65 (11.2), 44 (22.7).

Analytical: Calcd for C$_{14}$H$_{16}$O$_6$: C, 59.99; H, 5.75. Found: C, 60.04; H, 5.82.

EXAMPLE 16

To 100 ml of acetone was added 10.0 g (56.8 mmol) of L-galactono-1,4-lactone and 4 ml of concentrated sulfuric acid. This solution was stirred at room temperature for 21 hr. Ammonia was then bubbled through the solution until it was slightly basic. The white precipitate was filtered off and the solids washed twice with 50 ml of acetone. These washings were combined with the original filtrate and they were concentrated in vacuo to a yellow oil (12.0 g). This oil was chromatographed on 325 g of silica gel which was eluted with 10% ethyl acetate—chloroform to ethyl acetate. This afforded an oil which was triturated with diethyl ether and a white solid was filtered off. The solvent was removed from the filtrate affording 2.436 g (11.2 mmol, 20%) of an oil, 5,6-O-isopropylidene-L-galacto-1,4-lactone.

Alternatively 5,6-O-isopropylidene-L-galactono-1,4-lactone can be prepared by the following procedure: To 5 ml of dry dimethylformamide was added 2.10 g (11.8 mmol) of L-galactono-1,4-lactone, 1.0 g (11.8 mmol) of ethyl isopropenyl ether and a catalytic amount of p-toluenesulfonic acid. The reaction mixture was stirred at 0° for 1 hr and at room temperature for 18 hr. A small amount of Amberlite A-21 weakly basic resin was added and the reaction mixture was stirred for several minutes, filtered, and then concentrated in vacuo to an oil in which crystals formed on standing. Chromatography on 60 g of silica gel using 1% methanol—ethyl acetate as solvent afforded 1.213 g (5.56 mmol, 47%) of a clear oil which was pure by glpc: nmr (DMSO-d$_6$) $\delta_H$ 1.33 (s, 6, —CH$_3$), 3.60–4.47 (m, 6), 5.90–6.22 (m, 2, —OH); nmr (DMSO-d$_6$) $\delta_C$ 174.2 (—CO$_2$—), 108.9 (—OCO—), 79.2, 76.0, 73.8, 64.7 (—OCH—), 26.3, 25.6, (—CH$_3$); exact mass (C$_9$H$_{14}$O$_6$) (P+H) 219.0858 (calcd 219.0847), (P—CH$_3$) 203.0563 (calcd 203.0570).

To 17.5 ml of chloroform was added 4.263 g (19.5 mmol) of 5,6-O-isopropylidene-L-galactono-1,4-lactone and 3.2 ml of dry pyridine. The reaction mixture was cooled to −60°, and 1.39 ml (19.5 mmol) of acetyl chloride was slowly added. The reaction was stirred at −60° or below for 2 hr, diluted with ethyl acetate and extracted with 1N hydrochloric acid two times, water two times, saturated sodium bicarbonate two times, and brine. The organic solution was dried with sodium sulfate, and concentrated in vacuo to an oil, 3.79 g (15.2 mmol, 78%). This material clearly was a mixture of isomers by $^1$H-nmr with one isomer predominating. Analytically pure material was obtained by chromatography on silica gel (4% methanol-chloroform) followed by molecular distillation: nmr (DMSO-d$_6$) $\delta_H$ 1.31 (s, 6, —CH$_3$), 2.17 (s, 3, —COCH$_3$), 3.58–4.52 (m, 5), 5.65 (1, m, —CHOCOCH$_3$), 6.22 (1, m, —OH).

Analytical: Calcd for C$_{11}$H$_{16}$O$_7$: C, 50.76; H, 6.19. Found: C, 50.44; H, 6.11.

The material obtained from the above chromatography was greater than 95% one isomer. The nmr data suggests that it is 5,6-O-isopropylidene-3-O-acetyl-L-galactono-1,4-lactone.

The above crude mixture of acetates was converted to ascorbic acid as follows: To 25 ml of dry dichloromethane was added 1.69 ml (12 mmol) of trifluoroacetic anhydride. After cooling to less than −50°, 0.85 ml (12 mmol) of dimethylsulfoxide was added. The resulting heterogeneous solution was stirred at −50° or below for 30 min. Then 15 ml of dichloromethane containing 1.49 g (6.0 mmol) of the mixture of acetates was added. The resulting solution was stirred at less than −50° for 40 min at which time 1.2 ml of triethylamine was added. After 25 min at −50° or lower, the reaction mixture was stirred at room temperature for 1 hr. Ethyl acetate (100 ml) was added and the resulting solution was extracted two times with 1N hydrochloric acid (50 ml), two times with water (50 ml), and two times with brine (100 ml). The organic layer was dried over sodium sulfate and concentrated in vacuo to an oil, 1.25 g (5.08 mmol, 85%).

A portion of this oil (0.697 g, 2.7 mmol) was dissolved in 10 ml of 70% acetic acid—water and heat at 70° for 20 hr under nitrogen. The solvent was removed in vacuo affording 0.453 g of material. A portion was titrated with iodine and showed that ascorbic acid was formed in 50% yield (42% from the mixture of acetates). This material by tlc and glpc was identical with authentic ascorbic acid.

EXAMPLE 17

To a dry 500 ml flask fitted with a Dean-Stark trap was added 17.8 g (100 mmol) of L-gulono-1,4-lactone, 57 ml (400 mmol) of acetaldehyde diethyl acetal, 40 ml of dry dimethylformamide, 200 ml of benzene, and 0.2 g of p-toluenesulfonic acid. This reaction mixture was refluxed under nitrogen for 21 hr at which time a small amount of sodium bicarbonate was added. The solution was stirred for several minutes, cooled, and filtered. The solution was concentrated under vacuum to a light amber oil which was triturated with ether. The resulting solid, 5,6-O-ethylidene-L-gulono-1,4-lactone, (12.4 g, 60.8 mmol, 61%) which was pure by tlc was recrystallized from ethanol to afford 6.94 g (34 mmol, 34%) of a white crystalline solid, mp 153.5°–158.5°. A second crop of crystals weighing 1.22 g (6.0 mmol, 6%) was obtained by concentrating the mother liquor. Tlc on silica gel using ethyl acetate revealed that this material was a diastereomeric mixture. Recrystallization of this mixture from benzene afforded a crystalline product greatly enriched in one of the diastereomers, mp 164°–165°. The spectral data below was obtained from a diastereomeric mixture: ir (KBr) 3448, 3279, 1783 cm$^{-1}$; nmr (DMSO-d$_6$) $\delta_H$ 1.28 (two sets of d, 3, J = 5, -CH$_3$), 3.48–4.58 (m, 6), 5.00 (two sets of q, 1, J = 5, —OCHO—), 5.48 (broad d, 1, J = 4, —OH), 5.88 (d, 1, J = 7, —OH); nmr (DMSO-d$_6$) $\delta_C$ 176.0 (s, 1, —CO$_2$—), 81.6, 80.1; 75.6, 75.3; 70.5; 69.5, 69.0 (all d, 4), 65.4 (t, 1, —CH$_2$O—), 101.7, 100.4 (each a d, —OCHO—), 20.0, 19.6 (each a q, —CH$_3$); ms 203 (1.8), 189 (30.4), 125 (36.1), 87 (50.4), 69 (35.5), 60 (13.8), 59 (49.6), 58 (14.4), 57 (17.8), 55 (18.7), 45 (27.9), 44 (51.8), 43 (100), 42 (19.5), 41 (27.5).

Analytical: Calcd for C$_8$H$_{12}$O$_6$: C, 47.05; H, 5.92. Found: C, 47.09; H, 5.77.

To a solution of 3 ml of chloroform and 5 ml of dry pyridine under nitrogen was added 1.175 g (5.75 mmol) of 5,6-O-ethylidene-L-gulono-1,4-lactone. This solution was cooled to less than −50° and 0.57 ml (0.62 g, 6.05 mmol) of acetic anhydride was added. The reaction mixture was stirred at or below −50° for 3 hr and then at room temperature for 16 hr. Chloroform (100 ml) was added and the reaction mixture was extracted with 30 ml of water, two times with 30 ml of 1N hydrochloride acid and brine. The organic solution was dried with sodium sulfate and the solvent was removed in vacuo affording 1.118 g (4.5 mmol, 78%) of an oil which crystallized on standing. The nmr spectrum showed a mixture of the acetates.

To a 200 ml round-bottom flask under nitrogen was added 30 ml of dry dichloromethane. After cooling to less than −50°, 1.4 ml (2.1 g, 10 mmol) of trifluoroacetic anhydride followed by 0.71 ml (10 mmol, 0.78 g) of dry dimethylsulfoxide was added. The resulting heterogeneous solution was stirred at less than −50° for 30 min at which time the above mixture of acetates (1.118 g, 4.5 mmol) in 30 ml of dry dichloromethane was added while maintaining the temperature below −50°. The resulting homogeneous solution was stirred for 40 min below −50° and then 2 ml of dry triethylamine was added. After 25 min at −50° or lower, the solution was allowed to warm to room temperature and stirred for 2 hr. At that time 70 ml of ethyl acetate was added to the reaction mixture which was then extracted two times with 40 ml of 1N hydrochloric acid, once with 40 ml of water and brine. The organic layer was dried with sodium sulfate and concentrated in vacuo affording 0.992 g of material to which was added 10 ml of 70% acetic acid—water. This solution was heated for 20 hr under nitrogen at 80° ± 5°. Removal of the solvent afforded material which by tlc and glpc was identical with authentic ascorbic acid.

EXAMPLE 18

L-ascorbic acid may be prepared by the procedures of Examples 1 and 2 but employing each of L-galacto-1,4-lactone, L-talono-1,4-lactone and L-idono-1,4-lactone as starting materials.

EXAMPLE 19

D-ascorbic acid may be prepared by the procedures of Examples 1 and 2 but employing each of D-gulono-1,4-lactone, D-galacto-1,4-lactone, D-talono-1,4-lactone and D-idono-1,4-lactone as starting materials.

EXAMPLE 20

D-ascorbic acid may be prepared by the procedure of Example 5 but employing each of D-gulono-1,4-lactone and D-idono-1,4-lactone as starting materials.

EXAMPLE 21

To 9.41 g (52.9 mmol) of L-gulono-1,4-lactone was added 11.8 ml (0.211 mol) of acetaldehyde. Hydrogen chloride gas was bubbled through the reaction mixture which was then stirred at room temperature for 18 hours. The initially heterogeneous reaction mixture became a mobile liquid containing only a residual amount of solid which was removed by adding acetone and filtering. The solution was concentrated to an oil from which a crystalline solid was obtained on trituration with ethyl acetate. The resulting solid was recrystallized from ethyl acetate to afford 2.68 g (13.1 mmol, 25%) of material which was further purified by crystallization from ethanol, mp 158°–60°. Analytically pure 3,5-O-ethylene-L-gulono-1,4-lactone was obtained by recrystallization from acetone, mp 160°–62°: ir (KBr) 3367, 3175, 1799, 1779, cm$^{-1}$; nmr (DMSO-d$_6$) $\delta_H$ 1.53 (d, 3, J = 5, —CH$_3$), 3.58 (m, 2, —CH$_2$O—), 3.95 (m, 1), 4.17–5.17 (m, 5, —OH, —OCHO—, others), 5.87 (d, 1, J = 6, —OH); nmr (DMSO-d$_6$) $\delta_C$ 175.9 (—CO$_2$—), 96.2 (—OCO—), 75.6, 74.3, 70.6, 69.3 (—CHO—), 59.8 (—CH$_2$OH), 20.8 (—CH$_3$); ms 204 (0.3), 203 (1.6), 160 (22.3), 99 (21.8), 85 (34.4), 83 (11.3), 73 (27.5), 72 (11.6), 71 (27.7), 69 (11.1), 57 (39.3), 45 (100), 44 (11.3), 43 (50.7); exact mass (C$_8$H$_{12}$O$_6$), 204.0636 (calcd 204.0633).

Analytical: Calcd for C$_8$H$_{12}$O$_6$: C, 47.06; H, 5.93. Found: C, 47.44; H, 5.75.

To 6 ml of acetone was added 0.210 g (1.03 mmol) of 3,5-O-ethylidene L-gulono-1,4-lactone followed by 1.08 g (12.5 mmol) of manganese dioxide. The reaction mixture was stirred under nitrogen at room temperature for 2.25 hr. Acetone was added and the reaction mixture was filtered through a pad to celite to remove the manganese dioxide. 0.169 g (0.77 mmol, 75%) of 3,5-O-ethylidene-L-xylo-hexulosono-1,4-lactone hydrate was obtained on concentration of the acetone solution: ir (KBr) 3390, 1799 cm$^{-1}$; nmr (DMSO-d$_6$) $\delta_H$ 1.25 (d, 3, J = 5, —CH$_3$), 3.10–4.32 (m, 5), 4.43 (broad s, 1), 4.92 (m, 2, —OH and —CHCH$_3$), 7.07 and 7.38 (—C(OH)$_2$); extract mass (C$_8$H$_{10}$O$_6$), 202.0439 (calcd. 202.0477).

This material may be converted to ascorbic acid using the hydrolysis conditions described in Example 5.

EXAMPLE 22

To 8 ml of dry pyridine was added 1.254 g (4.71 mmol) of 3,5-O-benzylidene-L-gulono-1,4-lactone followed by 1.40 g (5.02 mmol) of triphenylchloromethane. The reaction was stirred at room temperature for 20 hr. Chloroform was added and the reaction mixture was extracted with water, 1N hydrochloric acid, saturated sodium bicarbonate, and brine. The chloroform extract was dried with sodium sulfate and concentrated affording an oil. Chromotography on florisil using 5% methanol—chloroform afforded 0.920 g (1.81 mmol, 38%) of 3,5-O-benzylidene-6-O-triphenylmethyl-L-gulono-1,4-lactone: ir (KBr) 3378, 1786 cm$^{-1}$; nmr (DMSO-d$_6$) $\delta_H$ 3.20 (m, 2), 4.27–4.93 (m, 4), 5.77 (s, 1, —OCHO—), 5.83 (broad peak, 1, —OH), 7.40 (broad singlet, 20, aromatic); nmr (DMSO-d$_6$) $\delta_C$ 175.5 (—CO$_2$—), 143.3, 137.5, 128.8, 128.2, 127.9, 127.8, 127.0, 126.2 (aromatic), 97.8 (—OCO—), 86.2, 74.7, 74.2, 70.6, 69.6, and 62.5 (—CO—); ms 508 (0.5), 259 (10.2), 258 (17.6), 249 (17.9), 244 (24.7), 243 (100), 165 (32.1), 107 (28.0), 105 (43.2), 79.0 (16.3), 77 (20.2); exact mass (C$_{32}$H$_{28}$O$_6$), 508.1939 (calc. 508.1886).

To 2 ml of acetone was added 0.071 g (0.14 mmol) of the above solid followed by 0.245 g (2.82 mmol) of manganese dioxide. The reaction was stirred at room temperature for 2 hrs. Acetone was added and the reaction mixture was filtered through a pad of celite to remove the manganese dioxide and concentrated (0.058 g, 0.11 mmol, 79%). To this material was added under nitrogen 2 ml of 70% acetic acid—water and the reaction mixture was heated to 70°–75° for 4 hr. The solvent was removed and afforded material which was identical with authentic ascorbic acid by tlc and glpc.

EXAMPLE 23

To 50 ml of benzene and 7 ml of dimethylformamide was added 10 ml (80 mmol) of cinnamaldehyde followed by two drops of polyphosphoric acid and 3.56 g (20 mmol) of L-gulono-1,4-lactone. The reaction mixture was refluxed and water removed via a Dean-Stark trap. After 5 hours this reaction mixture was filtered while hot. Sodium bicarbonate was added to the filtrate which was then refiltered. The solvent was removed under vacuum, the resulting oil triturated with ether and the solid formed was collected by filtration and dried to afford 2.44 g (8.4 mmol, 42%) of 3,5-O-cinnamylidene-L-gulono-1,4-lactone. Analytically pure material was obtained by trituration with hot benzene followed by recrystallization from water acetone, mp 164°–167° C. In an alternative procedure, the white solid resulting from ether trituration was purified by dissolving in tetrahydrofuran and washing the solution three times with a saturated brine-sodium bicarbonate solution. The tetrahydrofuran was then concentrated and the resulting solid was recrystallized from acetone-water, mp 185°–187° C, $[\alpha]_D^{24}$ + 39.4 (DMF); ir (KBr) 3450, 3227, 2860 and 1670 cm$^{-1}$; nmr (DMSO-d$_6$) $\delta_H$ 3.46–4.83 (m, 6), 5.0 (t, 1, J = 6, —CH$_2$OH), 5.37 (d, 1, J$_{AX}$ = 5, —OCHO—), 5.98 (d, 1, J = 6, —CHOH), 6.12 and 6.81 (AB of ABX, 2, J$_{AB}$ = 16, J$_{AX}$ = 5, J$_{BX}$ = 0, vinyl), 7.2–7.66 (m, 5, aromatic); ms. 292 (12.9), 133 (33.4), 132 (20.6), 131 (94.1), 127 (15.6), 115 (39.5), 107 (18.9), 105 (29.7), 104 (100), 103 (30.9), 91 (10.1), 78 (15.7), 77 (26.9), 57 (11.6), 55 (31.2), 51 (10.4), 43 (11.0).

Analytical: Calcd. for C$_{15}$H$_{16}$O$_6$: C, 61.63, H, 5.51. Found: C, 61.77; H, 5.52

What is claimed is:

1. A process for the preparation of ascorbic acid which comprises
    (a) contacting a 1,4-lactone selected from gulonolactone, galactonolactone, idonolactone and talonolactone with about three equivalents of a hydroxyl-protecting reagent per mole of 1,4-lactone;
    (b) contacting the resulting intermediate having a free hydroxyl group at the 2- or 3- position with an oxidizing agent effective to convert said hydroxyl group to a keto group; and (c) hydrolyzing the compound formed in step (b) until conversion to ascorbic acid is substantially complete.

2. The process of claim 1 wherein said hydroxyl-protecting reagent comprises a trialkylsilyl halide, wherein each alkyl is of 1 to 6 carbon atoms.

3. The process of claim 1 wherein said hydroxyl-protecting reagent comprises a dialkylsilyl halide, wherein each alkyl is of 1 to 6 carbon atoms.

4. The process of claim 1 wherein said hydroxyl-protecting reagent comprises an alkanoic anhydride of 3 to 8 carbon atoms.

5. The process of claim 1 wherein the hydroxyl-protecting reagent comprises an alkanoyl halide of 2 to 6 carbon atoms.

6. The process of claim 1 wherein said hydroxyl-protecting reagent comprises an aroyl halide wherein said aroyl is benzoyl, naphthoyl or monosubstituted benzoyl wherein said substituents are alkyl of 1 to 6 carbon atoms, alkoxy of 1 to 6 carbon atoms, halo or nitro.

7. The process of claim 1 wherein said hydroxyl-protecting reagent comprises a dialkyl ketone, wherein each alkyl is of 1 to 6 carbon atoms.

8. The process of claim 1 wherein said hydroxyl-protecting reagent comprises an alkyl aldehyde of 2 to 8 carbon atoms.

9. The process of claim 1 wherein said oxidizing agent is a sulfoxonium salt.

10. The process of claim 1 wherein said 1,4-lactone is gulonolactone.

11. The process of claim 2 wherein said trialkylsilyl halide is selected from a trimethylsilyl halide and a t-butyl-dimethylsilyl halide.

12. The process of claim 4 wherein said hydroxyl-protecting reagent is acetic anhydride.

13. The process of claim 5 wherein said alkanoyl halide is selected from acetyl chloride and acetyl bromide.

14. The process of claim 6 wherein said aroyl halide is selected from benzoyl chloride and benzoyl bromide.

15. The process of claim 7 wherein said dialkyl ketone is selected from acetone, methyl ethyl ketone and methyl isobutyl ketone.

16. The process of claim 8 wherein said alkyl aldehyde is selected from acetaldehyde and propionaldehyde.

17. A process for the preparation of ascorbic acid which comprises
   (a) contacting a 1,4-lactone selected from gulonolactone and idonolactone in the presence of an acid catalyst having a $pk_a$ of less than about 2.5 with at least about two equivalents of a hydroxyl-protecting reagent per mole of 1,4-lactone, said reagent being selected from an alkyl aldehyde of 2 to 8 carbon atoms; an aryl aldehyde, an arylalkyl aldehyde and an arylalkenyl aldehyde, wherein said aryl is phenyl, mono-substituted or di-substituted phenyl, wherein said substituents are alkyl of 1 to 6 carbon atoms, alkoxy of 1 to 6 carbon atoms, halo or nitro, and said alkyl and alkenyl are each of 2 to 4 carbon atoms;
   (b) contacting the resulting intermediate having a free hydroxyl group at the 2-position with an oxidizing agent effective to convert said hydroxyl group to a keto group;
   and (c) hydrolyzing the compound formed in step (b) until conversion to ascorbic acid is substantially complete.

18. The process of claim 17 wherein said alkyl aldehyde is isobutyraldehyde.

19. The process of claim 17 wherein said alkyl aldehyde is acetaldehyde.

20. The process of claim 17 wherein said aryl aldehyde is selected from benzaldehyde, o-methylbenzaldehyde, m-methylbenzaldehyde, 3,4-dichlorobenzaldehyde, o-methoxybenzaldehyde and o-chlorobenzaldehyde.

21. The process of claim 20 wherein said aryl aldehyde is benzaldehyde.

22. The process of claim 20 wherein said aryl aldehyde is o-methoxybenzaldehyde.

23. The process of claim 17 wherein said arylalkenyl aldehyde is cinnamaldehyde.

24. The process of claim 17 wherein said 1,4-lactone is gulonolactone.

25. The process of claim 17 wherein said oxidizing agent is manganese dioxide.

26. A compound of the formula

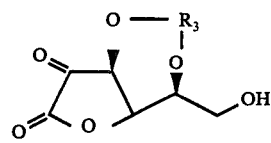

and the hydrated form thereof, wherein $R_3$ is a hydroxyl-protecting group derived from an alkyl aldehyde of 2 to 8 carbon atoms; an aryl aldehyde, an arylalkyl aldehyde or an arylalkenyl aldehyde, wherein said aryl is phenyl, mono-substituted or di-substituted phenyl, wherein said substituents are alkyl of 1 to 6 carbon atoms, alkoxy of 1 to 6 carbon atoms, halo or nitro, and said alkyl and alkenyl are each of 2 to 4 carbon atoms.

* * * * *